United States Patent [19]

Kaneko et al.

[11] Patent Number: 4,808,613

[45] Date of Patent: Feb. 28, 1989

[54] REBECCAMYCIN DERIVATIVE CONTAINING PHARMACEUTICAL COMPOSITION

[75] Inventors: Takushi Kaneko, Guilford; Henry S. Wong, Durham, both of Conn.; Jacob J. Utzig, Buffalo, N.Y.

[73] Assignee: Bristol-Myers Company, New York, N.Y.

[21] Appl. No.: 169,785

[22] Filed: Mar. 18, 1988

Related U.S. Application Data

[63] Continuation of Ser. No. 933,428, Nov. 21, 1986, abandoned.

[51] Int. Cl.$^4$ .............................................. A61K 31/40
[52] U.S. Cl. ....................................... 514/42; 514/43; 536/24
[58] Field of Search ...................... 536/22, 23; 514/42, 514/43

[56] References Cited

U.S. PATENT DOCUMENTS

4,487,925 12/1984 Nettleton et al. .................... 536/24
4,552,842 11/1985 Nettleton et al. .................... 435/75

OTHER PUBLICATIONS

Kaneko et al., Tetrahedron Letters, vol. 26(34), pp. 4015–4018, 1985.
Crom et al, Organic Chemistry, 2nd Edition, McGraw-Hill Book Co., N.Y., 1964.
Nettleton et al., Tetrahedron Letters, vol. 26(34), pp. 4011–4014, 1985.

*Primary Examiner*—Ronald W. Griffin
*Assistant Examiner*—L. Eric Crane
*Attorney, Agent, or Firm*—David M. Morse

[57] ABSTRACT

There are disclosed analogs of the antitumor agent, rebaccamycin, which possess antineoplastic properties against mammalian, particularly experimental animal, tumor systems. The compounds of the invention are aminoalkylated derivatives of rebeccamycin produced by first reacting rebeccamycin with a strong base to obtain a reactive intermediate and then reacting the reactive intermediate with an aminoalkyl compound.

1 Claim, No Drawings

REBECCAMYCIN DERIVATIVE CONTAINING PHARMACEUTICAL COMPOSITION

This application is a continuation of application Ser. No. 933,428, filed Nov. 21, 1987, now abandoned.

BACKGROUND OF THE INVENTION

1. Field of the Invention

This invention relates to novel compounds having antineoplastic properties, to their production, to a pharmaceutical composition containing an amount of at least one compound according to the invention which is effective to inhibit the growth of tumors in experimental animal systems, and to a method for therapeutically treating an experimental animal by administering an amount of at least one compound according to the invention which is effective to inhibit tumor growth in an experimental animal system.

2. Background Art

U.S. Pat. Nos. 4,487,925 and 4,552,842 disclose the anti-tumor agent designated rebeccamycin, and the 5'-N-methyl and 5',2",3",6"-tetraacetate derivatives thereof, and a process for producing the same agent by cultivating a rebeccamycin-producing strain of *Nocardia aerocolonigenes*, preferably *Nocardia aerocolonigenes* ATCC 39243, or a rebeccamycin-producing mutant thereof in an aqueous nutrient medium containing assimilable sources of carbon and nitrogen under submerged aerobic conditions until a substantial amount of rebeccamycin is produced.

SUMMARY OF THE INVENTION

This invention comprises analogs of the antitumor agent designated rebeccamycin (Formula I)

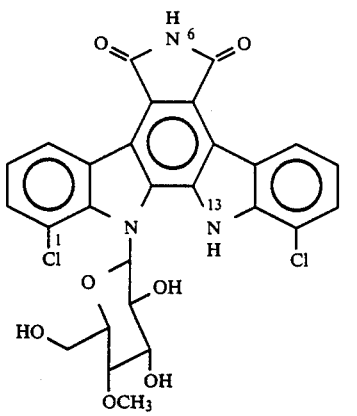

Formula I produced by first reacting rebeccamycin with a strong base to obtain a reactive intermediate and then reacting the reactive intermediate with an aminoalkyl halide. By the use of an amount of strong base slightly in excess, for example about 10% excess, of the molar equivalent amount of rebeccamycin followed by reacting the resulting intermediate with at least one molar equivalent based on rebeccamycin of an aminoalkyl halide as the alkylating agent, there is obtained the corresponding 6-aminoalkylrebeccamycin analog. By the use of an amount of strong base slightly in excess of two-times the molar equivalent amount of rebeccamycin, for example about 20% excess over two-times the molar equivalent amount of rebeccamycin, and then reacting the resulting intermediate with about one molar equivalent of an aminoalkyl halide as the alkylating agent, there is obtained the corresponding 13-aminoalkylrebeccamycin analog.

DETAILED DESCRIPTION OF THE INVENTION

In one generic aspect, this invention is a compound selected from the group consisting of the compounds having the formulas II and III below

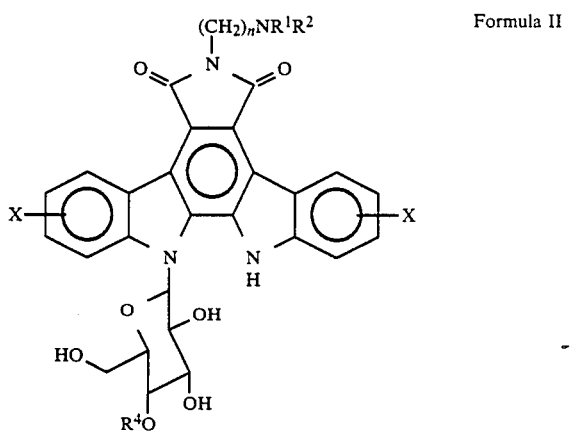

Formula II

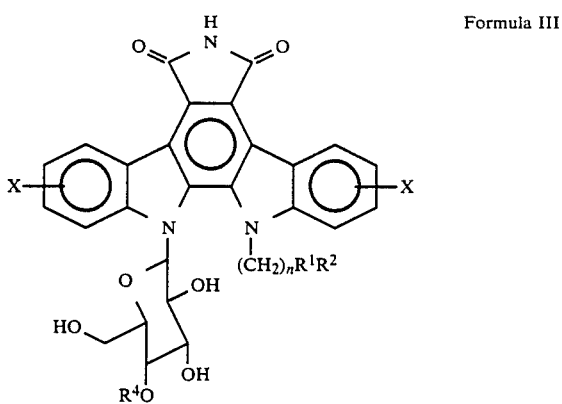

Formula III wherein:

n is an integer from 1 to 6;

$R^1$ and $R^2$, independently, are selected from hydrogen, unsubstituted and substituted $C_1$-$C_6$ alkyl, aralkyl having 1 to 3 carbons in the alkyl moiety and unsubstituted phenyl or phenyl substituted with 1 to 3 alkyl, alkoxy, hydroxy, halo, carboxyl, alkoxycarbonyl, and amino and mono- and di-lower-alkylamino groups in the aryl moiety, and aryl selected from unsubstituted phenyl and phenyl substituted with 1 to 3 alkyl, alkoxy, hydroxy, halo, amino, mono- and dialkylamino, nitro, carboxyl, alkoxycarbonyl, and cyano groups provided that both $R^1$ and $R^2$ are not each aryl and, when taken together, $R^1$ and $R^2$ may be selected from —$(CH_2)_4$— and $(CH_2)_2$—$R^3$—$(CH_2)_2$— to form a 5- or 6-membered ring together with the N-atom wherein $R^3$ is selected from $CH_2$, NH, O and S;

X is selected from H, F, Cl, Br, $C_1$-$C_3$ alkyl, OH, carboxyl, alkoxycarbonyl and alkoxy wherein the alkyl moiety is $C_1$-$C_3$ alkyl, benzyloxy, amino, mon- and dialkylamino; and $R^4$ is selected from H and $CH_3$; and pharmaceutically acceptable acid addition and base salts thereof.

Preferred, compounds according to this invention having one of Formulas II and III above are those wherein n is an integer from 1 to 6, $R^1$ and $R^2$, independently, are selected from unsubstituted and substituted $C_1$–$C_6$ alkyl and, when taken together, $R^1$ and $R^2$ may be selected from —$(CH_2)_4$— and —$(CH_2)_2$—$R^3$—$(CH_2)_2$— to form a 5- or 6-membered ring together with the N-atom wherein $R^3$ is selected from $CH_2$, NH, O and S, and wherein $R_4$ is H or $CH_3$ and X is selected from H, Cl, Br, OH, $OCH_3$ and $OCH_2C_6H_5$.

More preferred compounds according to this invention having one of Formulas II and III above are those wherein n is selected from the integers 1, 2 and 3; $R^1$ and $R^2$, independently, are selected from H, $C_1$–$C_3$ alkyl, and —$(CH_2)_4$—; $R^4$ is H or $CH_3$; and X is selected from H, Cl, Br, OH, $OCH_3$ and $OCH_2C_6H_5$.

Most preferred compounds according to this invention having one of Formulas II and III above are those wherein n is an integer selected from 2 and 3; X is Cl in each of the 1- and 11-positions of the ring system; $R^1$ and $R^2$ are each $C_2H_5$; and $R^4$ is H or $CH_3$.

The following Table 1 presents representative combinations of the many groups within the definition of X, n, $R^1$, $R^2$, $R^3$ amd $R^4$ and many further combinations of such groups will be readily apparent to those skilled in the art. It is to be understood that the aminoalkyl group, A, bearing the groups n, $R^1$ and $R^2$ may be substituted at either or both the 6- and 13-positions (designated $A^6$ and $A^{13}$) of the rebeccamycin ring system. Of course, when only one of $A^6$ or $A^{13}$ is aminoalkyl, the other is H.

TABLE 1

Representative Substituent Groups

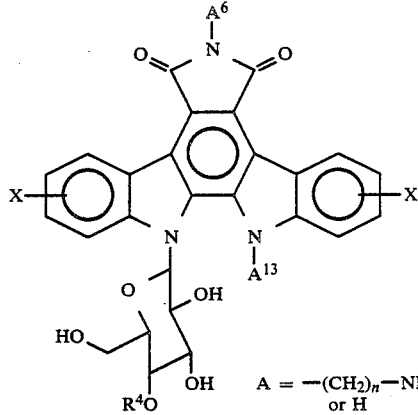

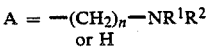

| X | n | $R^1$ | $R^2$ | $R^4$ |
|---|---|---|---|---|
| 1,11-dichloro | 2 | ethyl | ethyl | methyl |
| 1,11-dichloro | 3 | ethyl | ethyl | methyl |
| 3,9-diamino | 3 | methyl | methyl | H |
| 2,10-diamino | 4 | propyl | propyl | H |
| 3,9-dibenzyloxy | 5 | i-propyl | H | methyl |
| 4,8-dichloro | 6 | ethyl | H | methyl |
| 3,9-dichloro | 2 | phenethyl | H | methyl |
| 4,8-dihydroxy | 3 | benzyl | H | methyl |
| 3,9-dihydroxy | 2 | —$(CH_2)_4$— | | H |
| 4,8-dimethoxy | 3 | —$(CH_2)_2$—O—$(CH_2)_2$— | | methyl |
| 3,9-dimethoxy | 2 | —$(CH_2)_2$—NH—$(CH_2)_2$— | | methyl |
| 4,8-dimethyl | 3 | —$(CH_2)_5$— | | H |
| 3,9-dimethyl | 1 | —$(CH_2)_2$—S—$(CH_2)_2$— | | methyl |
| 2,10-dimethyl | 2 | hexyl | H | methyl |
| 3,9-dihydroxycarbonyl | 3 | ethyl | ethyl | methyl |
| 2,10-dibromo | 2 | —$(CH_2)_4$— | | methyl |
| H | 3 | ethyl | ethyl | H |

In other aspects, this invention is a pharmaceutical composition containing at least one of the compounds according to the invention and a method for therapeutically treating a mammalian host, for example, an experimental animal, affected by a malignant tumor by administering at least one of the compounds according to this invention in a tumor growth-inhibiting amount and, usually, by means of administering the compound in the form of the pharmaceutical composition.

By the expression "$C_1$–$C_6$ alkyl", more particularly unsubstituted $C_1$–$C_6$ alkyl, is meant straight-chain or branched-chain or cyclic alkyl groups having a total of six carbon atoms. Examples of suitable straight-chain alkyl groups include methyl, ethyl, propyl, butyl, pentyl and hexyl groups. Examples of suitable branched-chain alkyl groups include isopropyl, sec-butyl, t-butyl, 2-methylbutyl, 2-pentyl, 3-pentyl and the like groups. Examples of suitable cyclic alkyl groups include cyclopropyl, cyclobutyl, cyclopentyl and cyclohexyl groups. The alkyl groups may be substituted, generally with 1 or 2 substituents, with substituents selected from halo, hydroxy, alkoxy, amino, mono- and dialkylamino, nitro, carboxyl, alkoxycarbonyl, and cyano groups. By the expression "aralkyl" is meant benzyl, phenethyl (phenylethyl) and phenylpropyl groups wherein the phenyl moiety may be substituted. By the expression "aryl" is meant phenyl. The aralkyl or aryl group may contain substituted phenyl wherein the substituent may be from 1 to 3 alkyl, hydroxy, alkoxy, halo, amino, mono- and dialkylamino, nitro, carboxyl, alkoxycarbonyl, and cyano groups.

As used herein, the expression "halo" is meant in the conventional sense to include F, Cl, Br, and I.

When the expressions alkoxy, alkoxycarbonyl, mono- and dialkylamino are used, these expressions usually are meant to include an alkyl moiety having 1 to 3 carbon atoms.

As mentioned above, $R^1$ and $R^2$ are not each aryl. Also, $R^1$ and $R^2$ generally are not each selected from the sterically larger of the $C_1$–$C_6$ alkyl and from aralkyl groups. Preferably, when $R^1$ and $R^2$ are each alkyl, they are each selected from $C_1$–$C_3$ alkyl groups.

As is mentioned above, rebeccamycin is a known antitumor agent disclosed in U.S. Pat. Nos. 4,487,525 and 4,552,842. The Chemical Abstracts nomenclature for rebeccamycin is as follows: 5H-Indolo[2,3-a] pyrrolo[3, 4-c] carbazole-5,7 (6H)dione, 1, 11-dichloro-12, 13-dihydro-12-(4-O-methyl-beta-D-glucopyranosyl).

However, the name "rebeccamycin" is used throughout for simplicity although the Chemical Abstracts numbering systems is used to identify the various positions in the rebeccamycin ring system.

The starting material for the most preferred compounds according to this invention is rebeccamycin itself. Rebeccamycin, Formula I, may be produced by cultivating a rebeccamycin-producing strain of *Nocardia aerocolonigenes*, preferably a strain having the characteristics of *Nocardia aerocolonigenes* strain C38,383-RK2(ATCC39243) or a mutant thereof under submerged aerobic conditions in an aqueous nutrient medium as is described in U.S. Pat. Nos. 4,487,925 and 4,552,842.

Derivatives of rebeccamycin havin various groups substituted on the rebeccamycin ring system in place of the 1,11-dichloro substituents may be used as starting materials in the place of rebeccamycin to obtain compounds within the broad definition and preferred and more preferred embodiments according to the present invention. For example, didechlororebeccamycin can be produced by subjecting rebeccamycin to hydrogenolysis and the resulting intermediate may be subjected to alkylation using strong base followed by reaction of the intermediate from the strong base treatment with a suitable aminoalkyl halide. Other chromophores of rebeccamycin having various substituents on the rebeccamycin ring system can be produced using methods disclosed by T. Kaneko et al., *Tetrahedron Letters*, 26, 4015 (1985). For example, by using the procedures therein disclosed, compounds having the following formula, IV, were produced:

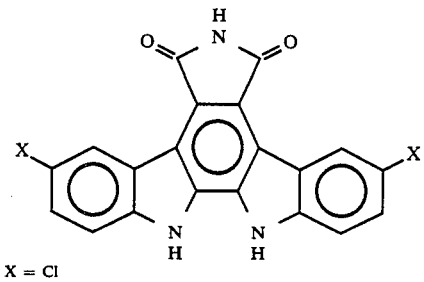

X = Cl
X = OCH$_3$
X = OCH$_2$Ph

The following more particularly describes a typical synthesis of compounds with chromophores similar or identical to that of rebeccamycin having various substituents on the ring system in the place of the Cl groups. Treatment of a substituted indole with methyl magnesium tetrahydrofuran produces a solution of indole Grignard (VI). Two equivalents of this solution and one equivalent of N-benzyloxymethyl 3,4-dibromo-maleimide gives an adduct of formula VII. This can be either photochemically cyclized by irradiation at 300 nm in a benzene solution containing a small amount of I$_2$ or thermally by refluxing a solution of the adduct in benzene in the presence of Ag$_2$O. The intermediate thus prepared (VIII) is then coupled with O-acylated 1-halosugar in the presence of Ag$_2$O to give N-glycoside IX. A catalytic hydrogenation to remove the N6 protecting group and a base hydrolysis of the sugar O-acyl groups gives the desired product X. Illustrative of the substituted indoles that can be used in this preparation are listed in Table 2.

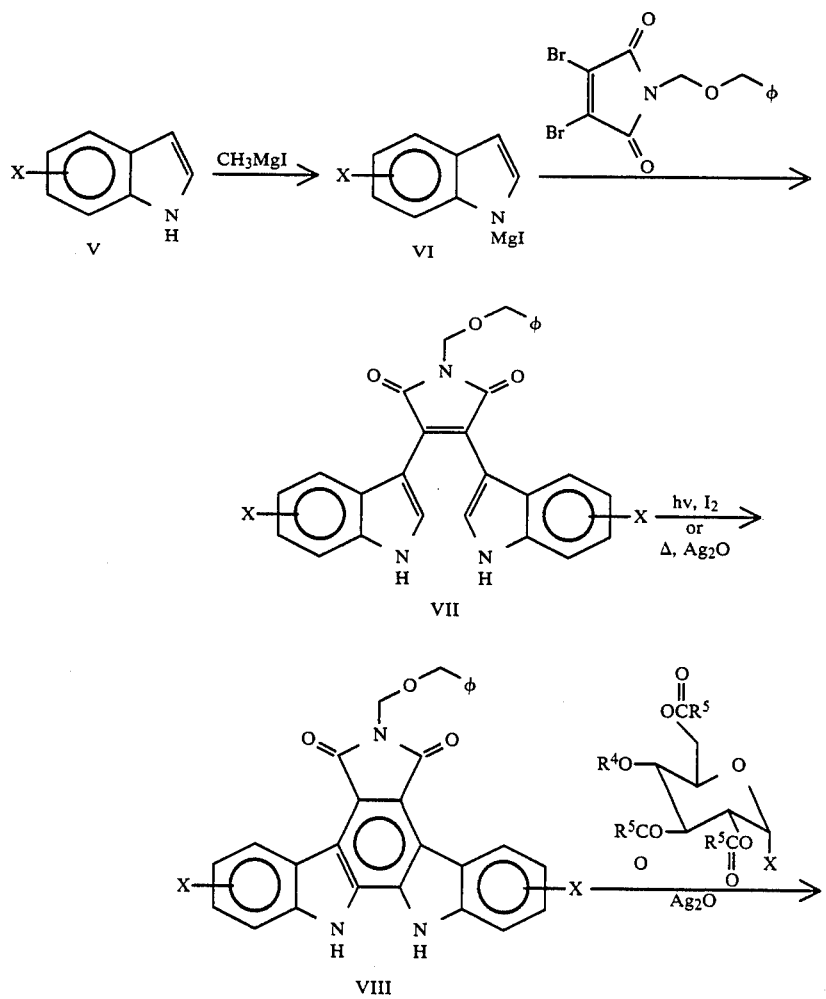

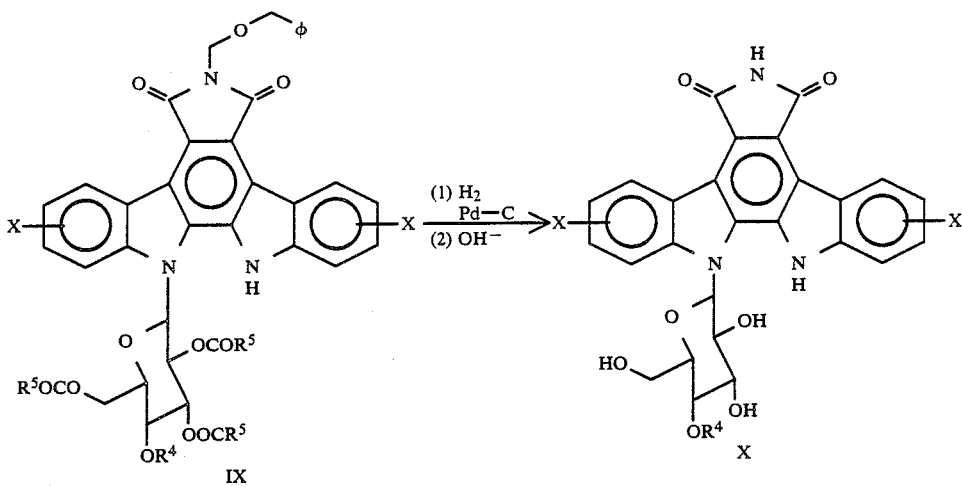

X and R⁴ are as defined herein
R⁵, typically is CH₃

Table 2—Starting Indoles

5-Aminoindole
6-Aminoindole
5-Benzyloxyindole
4-Chloroindole
5-Chloroindole
4-Hydroxyindole
5-Hydroxyindole
Indole
4-Methoxyindole
5-Methoxyindole
4-Methylindole
5-Methylindole
6-Methylindole
Indole-5-carboxylic acid Glycosidation of any one of the three chromophores represented by Formula IV or a chromophore represented by Formula X by reaction with an appropriate glycosyl halide provides a rebeccamycin derivative. And, reaction of the rebeccamycin derivative first with strong base followed by an aminoalkyl halide provides analogs of rebeccamycin according to this invention having one of Formulas II or III.

Having obtained rebeccamycin or a related compound with the same chromosphere this starting material is first dissolved in a suitable inert solvent, for example dimethylformamide (DMF), dimethylsulfoxide (DMSO), tetrahydrofuran (THF) or other anhydrous, aprotic solvent and then reacted with a strong base in an inert atmosphere, for example in an argon or nitrogen atmosphere. Although any strong base that is compatible with the starting material and solvent may be used, for example, $KNH_2$ or KH or $NaNH_2$ or NaH or lithium diisopropyl amide (LDA) or lithium hexamethyl disalazide or KOtBu or Grignard reagent such as MeMgBr or $NaNH_2$ or NaH or equivalent base, NaH may be advantageously employed.

It has been discovered that by using strong base, for example NaH, in an amount slightly in excess of the molar equivalent of the amount of starting material, for example in the range of from about 5% to about 15% and preferably about 10% (9-11%) excess, followed by treatment with at least one molar equivalent based on rebeccamycin starting material of an appropriate aminoalkyl compound, there may be obtained a compound according to the invention having an aminoalkyl substituent on the N-atom in the 6-position of the rebeccamycin ring system.

Further, it has been discovered that by using strong base, for example NaH, in a relatively large excess amount such as an amount slightly in excess of two-times the molar equivalent of the amount starting material, for example, in the range of about 15% to about 25% and preferably about 20% (18-22%) excess, followed by treatment with an appropriate aminoalkyl compound in an amount about the molar equivalent of starting material, there may be obtained a compound according to the invention having an aminoalkyl substituent on the N-atom in the 13-position of the rebeccamycin ring system.

When more than two equivalents of base are used, a dianion at N6 and N13 is formed. Since the N13 anion is more reactive than the N6 anion, a N13 aminoalkyl derivative is obtained when only one equivalent of aminoalkyl halide is used. When two equivalents of aminoalkyl halide is used, the N6,N13-diaminoalkyl derivative may be obtained.

Following the reaction of the starting material with a in situ with an appropriate reactive aminoalkyl compound by adding the aminoalkyl compound to the mixture of starting material and strong base and intermediate reaction product threof in inert solvent. Any aminoalkyl compound that is compatible with the starting material and product and solvent may be used, for example an aminoalkyl halide or sulfonate and the like, represented by the formula $L\text{-}(CH_2)_n\text{---}NR^1R^2$ wherein n, $R^1$ amd $R^2$ are as defined above and L is a leaving group such as halide or methanesulfonate or p-toluenesulfonate. Generally an aminoalkyl halide such as, for example, diethylaminoethyl chloride and diethylaminopropyl chloride, may be advantageously employed.

Generally, the reaction of strong base with starting material may be carried-out advantageously at about room temperature, that is, at about 18° C. to about 22° C. The mixture of starting material and strong base, generally, may be stirred for a period of a few minutes to several hours; however, the reaction is usually complete in about 20-30 minutes.

Then, there is added to the stirred mixture of starting material and strong base and resulting reactive intermediate reaction product thereof in inert solvent the appropriate aminoalkyl compound and the resulting mixture may be stirred at room temperature for about 20–24 hours or at about 4° C. for a shorter period of time, for example, six hours until the reaction of the reactive intermediate with aminoalkyl compound is complete.

The compounds of Formulas II and III according to this invention may be provided as pharmaceutically acceptable acid addition and base salts provided that the anion or cation thereof did not contribute significantly to the toxicity of the salt and that the salts are compatible with the standard and conventional pharmaceutical carriers and other conventional adjuvants and excipients customarily employed in producing pharmaceutical compositions adapted for oral or parenteral administration. The acid addition salts are formed by conventional techniques involving reaction of compounds of Formulas II and III with a mineral acid or organic carboxylic and sulfonic acids. Examples of suitable mineral acids include hydrochloric acid, phosphoric acid, and the like. Examples of suitable organic acids include acetic acid, citric acid, maleic acid, succinic acid, benzoic acid, tartaric acid, ascorbic acid, methanesulfonic acid, p-toluenesulfonic acid, and the like.

The base salts are formed by conventional techniques involving reaction of the compounds of Formulas II and III with alkali (Na, K) and alkalkine earth (Ca, Zn, Ba, Mg, and Mn) metal bases, more preferably with alkali metal bases, and by reaction with amines. Suitable bases include the hydroxide, carbonate or bicarbonate salts of the metals mentioned above such as, for example, sodium and potassium hydroxides, sodium and potassium carbonates, and sodium and potassium bicarbonates and the corresponding calcium and zinc salts. Additional suitable bases include ammonium salts those formed by reaction of compounds of formulas II and III with triethylamine, dibenzylamine, N, N'-dibenzylethylenediamine, procaine, and equivalent amines.

The pharmaceutical carrier may be solid or liquid to provide solid or liquid compositions. Solid form compositions suitable for oral administration include powders, tablets, capsules, caplets, dispersible granules, and cachets. Suitable solid carriers include at least one carrier substance which may function only as a carrier or may in addition serve a further function such as a diluent, flavoring agent, solubilizer, lubricant, suspending agent, binder, tablet disintegrating agent, encapsulating agent and te like. Inert solid carriers include, to name but a few, magnesium carbonate and stearate, talc, sugar, lactose, pectin, dextrin, starch, gelatin, cellulosic materials, and the like. The compounds according to the invention may be provided as sterile soluble compounds or compositions, including solutions and suspensions and emulsions, thereof which can be dissolved in sterile water or other liquid medium for oral administration or for parenteral administration. Examples of liquid carriers suitable for oral administration include water, alcohol, polypropylene glycol, polyethylene glycol and mixtures of two or more of the above. Examples of liquid carriers suitable for parenteral use include water-for-injection, physiological aline, and other suitable sterile injection media. Suitable buffers for use with the liquid carrier to provide, generally, a suitable buffered isotonic solution include trisodium orthophosphate, sodium bicarbonate, sodium citrate, N-methylglucamine, L(+)-lysine, and L(+)-arginine to name but a few representative buffering agents.

The pharmaceutical composition will contain an amount of active component, that is, compound of Formula II or III or mixture thereof, which may be varied or adjusted widely depending upon the particular application, the form, the potency of the particular compound used, and the desired concentration of compound in the composition. Generally, the amount of active component will range between about 0.5–90% by weight based on total weight of composition.

In therapeutic use for treating a mammalian host, for example an experimental animal host, affected by a malignant tumor, the compounds of this invention will be administered in an amount effective to inhibit the growth of the tumor, that is, a tumor growth-inhibiting amount of dosage. Generally, the tumor growth-inhibiting amount will be in the range of about 0.1 to about 15 mg/kg of animal body weight/day. It is to be understood that the actual preferred dosage of compound will vary widely depending upon the requirements of the animal being treated, the particular animal host and situs and disease being treated, the composition being used, and the route of administration. Many factors that modify the action of the anti-neoplastic agent will be taken into account by one skilled in the art to which this invention pertains including, for example, age, body weight and sex of the animal host; diet; time of administration; rate of excretion; condition of the host; severity of the disease; and the like. Administration may be carried out simultaneously or periodically within the maximum tolerated dose. Optimal administration (or application) rates for a given set of conditions may be readily ascertained by those skilled in the art using conventional dosage determination tests.

The following examples are presented to illustrate but a few representative embodiments of this invention and are not to be construed as limiting in scope. All parts and percentages are by weight and all temperatures are in degrees Celsius unless otherwise indicated.

Rebeccamycin analogs according to this invention were tested for antitumor activity against the transplanted mouse leukemia P-388 according to the procedures of Geran et al. reported in *Cancer Chemother. Rpts.*, 3, 1–103 (1972). Prolongation of survival of leukemic mice was observed at several dosage levels ranging from 6 mg/kg body wt/day to 100 mg/kg body wt./day. Results of the tests are shown in the accompanying Table 3. The standard, comparison agent is selected from olivomycin and mitomycin C. These results illustrate that the rebeccamycin analogs according to the invention possess useful antineoplastic activity.

EXAMPLE 1. 6-(2-Diethylaminoethyl)rebeccamycin

DMF (100 mL) was added under argon to a mixture of rebeccamycin (990 mg, 1.74 mmol) and NaH (46 mg, 1.91 mmol). After 20 minutes of stirring at room temperature, 2-diethylaminoethyl chloride (524 mg, 3.86 mmol) was added.

The resulting mixture was stirred for 24 h. and the reaction was then quenched by addition of 1% aq HCl solution. The reaction mixture was basified by addition of saturated $NaHCO_3$ solution and extracted with EtOAc.

The organic layer was collected and washed with brine and dried over $Na_2SO_4$. The residue obtained by evaporation of the solvent was chromatographed on silica gel (elution with EtOAc) to give 770 mg (66%) of the title compound: mp>250° C.; NMR (DMSO-d$_6$) δ 10.68 (s, 1H), 9.26 (d, 1H, J=7.8 Hz), 9.08 (d, 1H, J=7.9 Hz), 7.73 (d, 1H, J=8.9 Hz), 7.70 (d, 1H, J=8.9 Hz), 7.45 (t, 2H, J=7.8 Hz), 6.94 (d, 1H, J=9.1 Hz), 5.43 (d, 1H, J=5.6 Hz), 5.31 (bs, 1H), 5.03 (d, 1H J=5.7 Hz), 395 (s, 2H), 3.82 (m, 2H), 3.70-3.48 (m, 7H), 2.72 (m, 2H), 2.53 (m, 4H), 0.94 (t, 6H, J=7.0 Hz); IR (KBr) 3343, 1692, 1381, 1070, 760 cm$^{-1}$; FABMS 669 (M+1), 493, 217 m/e.

EXAMPLE 2. 6-(2-Diethylaminoethyl)rebeccamycin hydrochloride

To a solution of 6-(2-diethylaminoethyl)rebeccamycin (770 mg, 1.15 mmol) in 30 mL of THF at 0° C. was added one equivalent of 5.6M ethanolic HCl solution. After stirring 3 h at 0° C. the resulting precipitate was collected by filtration and washed with diethyl ether to give 728 mg (90%) of the title compound: mp >250° C.; NMR (DMSO-d$_6$) δ10.7 (s, 1H), 10.16 (s, 1H), 9.23 (d, 1H, J=8.1 Hz), 9.05 (d, 1H, J=8.0 Hz), 7.74 (d. 1H, J=8.5), 7.72 (d, 1H, J=9.3 Hz), 7.46 (t, 2H, J=8.1 Hz), 6.94 (d, 1H, H=9.1 Hz), 5.47 (bs, 1H), 5.36 (bs, 1H), 5.08 (bd, 1H, J=3.8 Hz), 4.11 (t, 2H, J=6.3 Hz), 3.97 (bs, 1H), 3.85 (d, 1H, J=9.5 Hz), 3.66-3.57 (m, 7H), 3.49-3.20 (m, 7H), 1.26 (t, 6H, J=7.0 Hz); IR (KBr) 3336, 1699, 1416, 1381, 1084, 760 cm$^{-1}$; FABMS 669 (M+1), 635, 493 m/e.

EXAMPLE 3. 6-(3-Diethylaminopropyl)rebeccamycin

DMF (20mL) was added under argon to a mixture of rebeccamycin (162 mg, 0.28 mmol) and NaH (7.5 mg, 0.31 mmol). To this solution was added 110 mg (0.78 mmol) of 3-diethylaminopropyl chloride. The resulting solution was stirred and warmed to 40° C. for 6 h. A workup similar to Example 1 gave 55 mg (28%) of the title compound: NMR (DMSO-d$_6$) δ 5 9.28 (d, 1H, J=7.8 Hz), 9.10 (d, 1H, J=8.1 Hz), 7.73 (d, 1H, J=9.4 Hz), 7.70 (d, 1H, J=9.4 Hz), 7.45 (d, 1H, J=7.8 Hz), 6.94 (d, 1H, J=9.1 Hz), 5.42 (bd, 1H, J=5.8 Hz), 5.31 (bs, 1H), 5.03 (bs, 1H), 3.95 (bs, 2H), 3.82-3.59 (m, 9H), 2.44 (m, 6H), 1.81 (m, 2H), 0.90 (t, 6H, J=7.0 Hz); IR (KBr) 3328, 1691, 1376, 1052, 755 cm$^{-1}$; MS 682 (M), 653, 403, 393 m/e.

EXAMPLE 4. 6-(3-Diethylaminopropyl)rebeccamycin hydrochloride

Treatment of the product from Example 3 with ethanolic HCl in a similar manner as Example 2 gave the title compound in 89% yield: mp>250° C.; NMR (DMSO-d$_6$) δ 5 10.70 (s, 1H), 9.81 (bs, 1H), 9.26 (d, 1H, J=7.1 Hz), 9.09 (d, 1H, J=8.0 Hz), 7.73 (d, 1H, J=11.4 Hz), 7.72 (d, 1H, J=11.0 Hz), 7.43 (t, 2H, J=7.9 Hz), 6.94 (d, 1H, J=9.2 Hz), 5.46 (bs, 1H), 5.34 (bs, 1H), 5.06 (bs, 1H), 3.95 (bs, 2H), 3.83 (m, 2H), 3.66-3.54 (m, 5H), 3.20 (m, 2H), 3.10 (m, 4H), 2.12 (m, 2H), 1.18 (t, 6H, J=7.2 Hz); IR (KBr) 3343, 1692, 1452, 1070, 760 cm$^{-1}$; FABMS 683, (M+1), 507, 406 m/e.

EXAMPLE 5. 13-(3-Dethylaminopropyl)rebeccamycin

DMF (25 mL) was added under argon to a mixture of rebeccamycin (188 mg, 0.33 mmol) and NaH (17 mg 0.73 mmol). After a few minutes of stirring at room temperature, 3-diethylmainopropyl chloride (54 mg, 0.36 mmol) was added and the resulting solution was stirred at room temperature for 22 h. The reaction was quenched by addition of 10% HCl solution in water. Saturated NaHCO$_3$ solution was added to basify the solution and the product was extracted with EtOAc. The organic layer was collected and washed with brine and dried over MgSO$_4$. The residue obtained after evaporation of the solvent was chromatographed on neutral alumnina (10% MeOH-acetone) to give 76 mg (34%) of the title compound: mp 203°-204° C.; NMR (DMSO-d$_6$) δ 10.67 (s, 1H), 9.28 (d, 1H, J=8.1 Hz), 9.10 (d, 1H, J=8.1 Hz), 7.73 (d, 1H, J=10.9 Hz), 7.71 (d, 1H, J=11,6 Hz), 7.45 (t, 2H, J=8.1 Hz), 6.94 (d, 1H, J=9.0 Hz), 5.43 (d, 1H, J=5.8 Hz), 5.32 (t, 1H, J=5.2 Hz), 5.03 (D, 1H, J=5.5 Hz), 3.96 (m, 2H), 3.85-3.79 (m, 3H), 3.91-3.53 (m, 5H), 2.71 (m, 4H) 1.95 (m, 2H), 1.13 (m, 6H); IR (KBr) 3343, 1696, 1388, 1085, 760 cm$^{-1}$; MS 683 (M+1), 654, 506 m/e.

TABLE 3

EFFECT OF REBECCAMYCIN ANALOGS ON P-388 LEUKEUMIA

| Compound | Dose, IP mg/kg/inj | Median Survival Time (MST) Days | % T/C | Avg. wt. change, gm day 4 |
|---|---|---|---|---|
| Olivomycin | 0.8 | 17.0 | 162 | −2.4 |
|  | 0.4 | 13.5 | 129 | −2.6 |
| Ex. 1 | 100 | 13.0 | 124 | −2.0 |
|  | 50 | 17.5 | 167 | −2.2 |
|  | 25 | 14.0 | 133 | −0.5 |
| Mitomycin C | 4.8 | 19.0 | 211 | −2.0 |
|  | 3.2 | 22.0 | 244 | −1.5 |
| Ex. 2 | 8.0 | 12.0 | 133 | −0.4 |
|  | 6.0 | 12.5 | 139 | −0.0 |
| Ex. 4 | 8.0 | 12.5 | 139 | −0.9 |
|  | 6.0 | 13.0 | 144 | 0.1 |

What is claimed is:

1. A pharmaceutical composition comprising a tumor growth-inhibiting amount of about 0.5-90% by weight based on total weight of composition of at least one compound selected from the group of compounds having the formulas

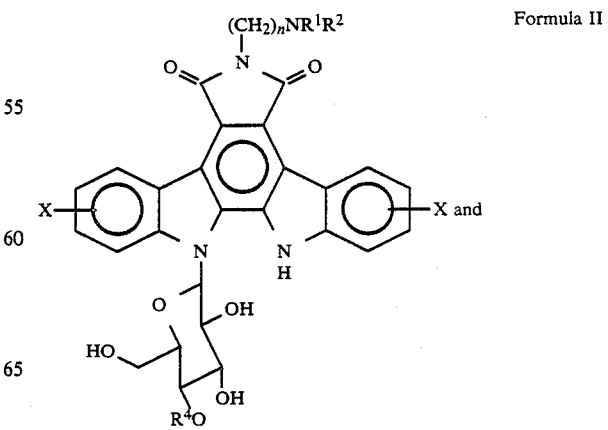

Formula II

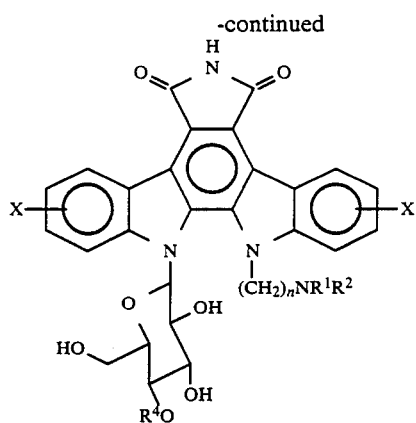

Formula III wherein n is an integer from 1 to 6;

R¹ and R², independently, are selected from hydrogen, unsubstituted and substituted $C_1$-$C_6$ alkyl, aralkyl having 1 to 3 carbons in the alkyl moeity and unsubstituted phenyl or phenyl substituted with 1 to 3 alkyl, alkoxy, hydroxy, halo, carboxyl, alkoxycarbonyl and amino and mon- and di-loweralkylamino groups in the aryl moiety, and aryl selected from unsubstituted phenyl and phenyl substituted with 1 to 3 alkyl, alkoxy, hydroxy, halo, amino, mono- and dialkylamino, nitro, carboxyl, alkoxycarbonyl and cyano groups provided that both R¹ and R² are not each aryl and, when taken together, R¹ and R² may be selected from —$(CH_2)_4$— and $(CH_2)_2$—$R^3$—$(CH_2)_2$— to form a 5- or 6-membered ring together with the N-atom wherein R³ is selected from $CH_2$, NH, O and S;

X is selected from H, F, Cl, Br, $C_1$-$C_3$ alkyl, OH, carboxyl, alkoxycarbonyl and alkoxy wherein the alkyl moiety is $C_1$-$C_3$ alkyl, and benzyloxy; and R⁴ is selected from H and $CH_3$; and pharmaceutically acceptable acid addition and base salts thereof, and a pharmaceutically acceptable carrier.

* * * * *